US00PP37251P2

(12) United States Plant Patent
Ibarra

(10) Patent No.: US PP37,251 P2
(45) Date of Patent: Feb. 10, 2026

(54) ***CORNUS* PLANT NAMED 'Elsie Red'**

(50) Latin Name: *Cornus florida*
Varietal Denomination: Elsie Red

(71) Applicant: Roman Martinez Ibarra, Huntland, TN (US)

(72) Inventor: Roman Martinez Ibarra, Huntland, TN (US)

( * ) Notice: Subject to any disclaimer, the term of this patent is extended or adjusted under 35 U.S.C. 154(b) by 0 days.

(21) Appl. No.: 19/255,767

(22) Filed: Jun. 30, 2025

(51) Int. Cl.
*A01H 5/00* (2018.01)
*A01H 6/00* (2018.01)

(52) U.S. Cl.
USPC ..... Plt./220
CPC ..... *A01H 6/00* (2018.05)

(58) Field of Classification Search
USPC ..... Plt./220
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Cornus florida* plant named 'Elsie Red' that is characterized by its flowers that are bright red-pink in color (bracts) with yellow centers, its rapid growth habit, its good resistance to powdery mildew, and its flowers that are sturdy and have a high tolerance to wind.

2 Drawing Sheets

Botanical classification: *Cornus florida*.
Variety denomination: 'Elsie Red'.

BACKGROUND OF THE INVENTION

The present invention relates to a new and distinct cultivar of *Cornus florida* plant and will be referred to hereafter by its cultivar name, 'Elsie Red'. 'Elsie Red' is a new cultivar of dogwood, a shrub grown for use as an ornamental landscape plant.

The Inventor discovered the new cultivar as a chance seedling growing in a production field at his nursery in Huntland, Tennessee in August of 2017. The field had been planted with seed from unnamed and unpatented plants of *Cornus florida*.

Asexual propagation of the new cultivar was first accomplished by the Inventor using budding onto seedlings (not patented) of *Cornus florida* in August of 2017 in Huntland, Tennessee. Asexual propagation of the new cultivar by budding has determined that the characteristics are stable and are reproduced true to type in successive generations.

SUMMARY OF THE INVENTION

The following traits have been repeatedly observed and are determined to be the characteristics of the new cultivar. These attributes in combination distinguish 'Elsie Red' as a unique cultivar of *Cornus*.

1. 'Elsie Red' exhibits flowers that are bright red-pink in color (bracts) with yellow centers.
2. 'Elsie Red' exhibits good branching with a strong central leader.
3. 'Elsie Red' exhibits a rapid growth habit.
4. 'Elsie Red' exhibits good resistance to powdery mildew.
5. 'Elsie Red' flowers that are sturdy and have a high tolerance to wind.

The probable female and male parents of 'Elsie Red' differ from 'Elsie Red' in having white color flowers as all the plants in the production field had white flowers. 'Elsie Red' can be most closely compared to the cultivars of *Cornus florida* 'JN13' (U.S. Plant Pat. No. 29,424) and 'Comco No. 1' (U.S. Plant Pat. No. 10,166). 'JN13' is similar to 'Elsie Red' in having red color flowers (bracts). 'JN13' differs from 'Elsie Red' in having flowers (bracts) that are more burgundy and less bright in color and less sturdy so prone to shattering in the wind, and branches and central leader that are weaker. 'Comco No. 1' is similar to 'Elsie Red' in having red color flowers (bracts) and a rapid growth habit. 'Comco No. 1' differs from 'Elsie Red' in having flowers (bracts) that are lighter red in color and less sturdy so prone to shattering in the wind.

BRIEF DESCRIPTION OF THE DRAWINGS

The accompanying color photographs illustrate the overall appearance and distinct characteristics of the new *Cornus*. The photographs were taken of a three year-old plant as grown in a trial field in Huntland, Tennessee.

The photograph in FIG. 1 provides a side view of a plant of 'Elsie Red' in bloom.

Figure 1:
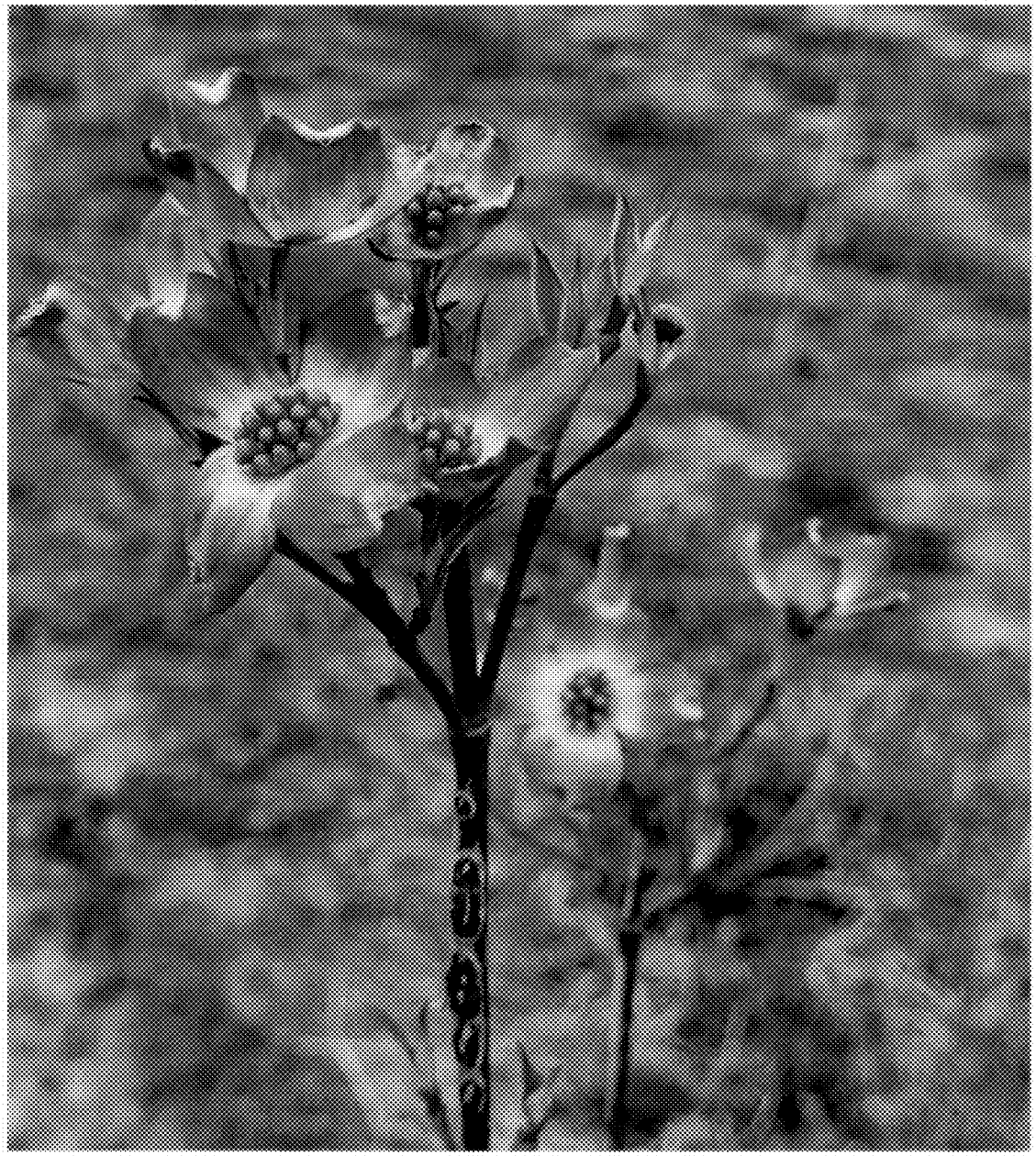
Figure 2:
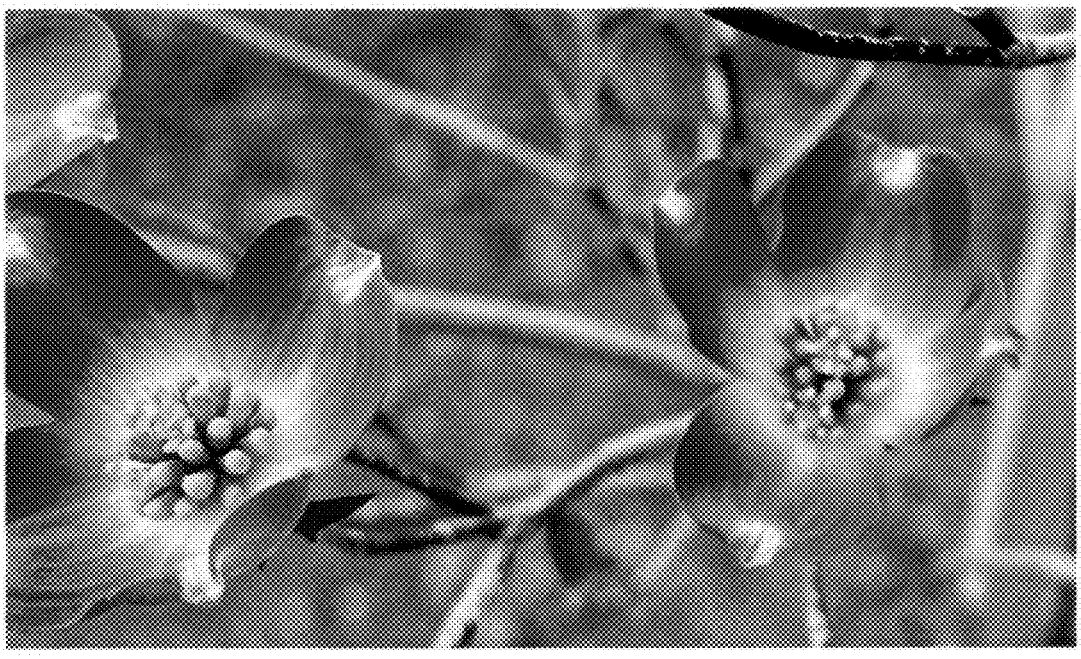

The photograph in FIG. 2 provides a close-up view of flowers of 'Elsie Red'.

The colors in the photographs are as close as possible with the photographic and printing technology utilized and the color values cited in the detailed botanical description accurately describe the colors of the new *Cornus*.

DETAILED BOTANICAL DESCRIPTION

The following is a detailed description of three year-old plants of the new *Cornus* as grown in 10-gallon containers in Huntland, Tennessee. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms in early spring for 2 to 3 weeks in Tennessee.

*Plant type*.—Deciduous shrub.

*Plant habit*.—Upright with strong central leader.

*Plant height and spread*.—Reaches up to 7.62 m in height, 6 m in spread as a mature tree in the landscape and 1.2 m in height and 60 cm in spread in a 10-gallon container.

*Diseases and pests*.—High resistance to powdery mildew (most typically caused by *Erysiphe pulchra*). No resistance to pests.

*Cold hardiness*.—At least in U.S.D.A. Zones 5 to 8.

*Root description*.—Fibrous and fine, N158A in color.

*Propagation*.—Budding.

*Time to develop a young plant*.—1 year from budding to produce a fully rooted liner.

*Growth rate*.—Vigorous.

Branch description:

*Branch shape*.—Rounded.

*Branch color*.—Young; 145A, maturing wood and bark; 200A and 198D.

*Branch size*.—Central leader; 30 cm in length and 5 cm in diameter, measured 60 cm above the soil level, lateral branches; up to 60 cm in length and 7 mm in diameter.

*Branch surface*.—New growth; smooth, dull, mature stems and bark; glabrous and bark-like.

*Internode length*.—An average of 15 cm in length.

*Branching*.—Main branch; 1, lateral branches; 20 per main branch, tertiary branches; 8 per lateral branch.

Foliage description:

*Leaf shape*.—New leaves; lanceolate, mature leaves; oval to elliptic.

*Leaf length*.—About 6 cm.

*Leaf width*.—About 2.5 cm.

*Leaf division*.—Simple.

*Leaf base*.—Cuneate to oblique.

*Leaf apex*.—Acuminate.

*Leaf fragrance*.—None.

*Leaf venation*.—Pinnate, color matches leaf colors.

*Leaf margins*.—Entire and slightly undulate.

*Leaf arrangement*.—Opposite.

*Leaf attachment*.—Petiolate.

*Leaf texture* (*both surfaces*).—Smooth and moderately pubescent.

*Leaf color* (*both surfaces*).—138A, flushed with 183A.

*Petioles*.—Average of 1.5 cm in length, 2 mm in diameter, glossy and glabrous surface, 145A in color.

*Stipules*.—Linear in shape, an average of 5 mm in length and 2 mm in width, acute apex, truncate base, color; 138A and 183A, becoming 183A when mature.

Inflorescence description:

*Inflorescence type*.—Pseudanthium; clusters of apetalous flowers surrounded by showy petal-like involucral bracts.

*Lastingness of inflorescence*.—2 to 3 weeks.

*Inflorescence size*.—An average of 6.5 cm in diameter, 1 cm in depth.

*Inflorescence quantity*.—Average of 30.

*Flower fragrance*.—Faintly pleasant.

*Flower quantity*.—An average of 20 per inflorescence.

*Flower type*.—Rotate, florets.

*Flower size*.—3 mm in depth, 4 mm in diameter.

*Flower buds*.—Oblong in shape, an average of 3 mm in length and 1.5 mm in width, surfaces are smooth and glabrous, color; young buds 145A, before burst 11C.

*Involucral Bracts* (*showy*).—4, base fused to top of calyx, spreading, cup-shaped and curling upwards, oblong in shape, 3 cm in length and 2.5 cm in width, margins entire, apex cuspidate, both surfaces have striations, matte, and velvety, color; when opening and fully open upper surface a blend of 60A, 63A and 63B, blending into base N155A and tips NN155A, when opening and fully open lower surface a blend of 54C and NN155D, lightly flushed with 145B, base and tips NN155D.

*Peduncles*.—1 mm in length, 0.5 mm in diameter, slightly glossy surface, 145A in color.

*Pedicels*.—None.

*Sepals*.—4, cuneate base, fused, cup-shaped to curled, acute apex, 3 mm in length and 1 mm in width, striated surfaces, translucent and slightly glossy, color (both surfaces); 145A, apex 20B.

Reproductive organs:

*Gynoecium*.—Pistil; 1, up to 1 mm in length, 0.5 mm in diameter, style and stigma; not distinguishable, 144A in color, ovary; round, superior, 1 mm in diameter, 143A in color.

*Androecium*.—Stamens; 4, 4 mm in length, exserted beyond corolla, filaments; 4 mm in length, 0.4 mm in diameter, 144C in color, glossy surface, anthers; 0.7 mm in diameter, club-shaped, 20B in color, pollen; high in quantity and 20B in color.

*Fruit and seed*.—Have not been observed to date.

It is claimed:

1. A new and distinct cultivar of *Cornus florida* plant named 'Elsie Red' as herein illustrated and described.

* * * * *